(12) United States Patent
Low et al.

(10) Patent No.: US 9,738,627 B2
(45) Date of Patent: Aug. 22, 2017

(54) METHOD FOR SYNTHESIZING 2,6-BIS[3'-(N-CARBAZOLYL)PHENYL] PYRIDINE COMPOUND

(71) Applicants: BEIJING AGLAIA TECHNOLOGY DEVELOPMENT CO., LTD., Beijing (CN); GUANGDONG AGLAIA OPTOELECTRONIC MATERIALS CO., LTD., Foshan, Guangdong (CN)

(72) Inventors: Kam-hung Low, Foshan (CN); Lifei Cai, Beijing (CN)

(73) Assignees: BEIJING AGLAIA TECHNOLOGY DEVELOPMENT CO., LTD., Beijing (CN); GUANGDONG AGLAIA OPTOELECTRONIC MATERIALS CO., LTD., Foshan (CN)

( * ) Notice: Subject to any disclaimer, the term of this patent is extended or adjusted under 35 U.S.C. 154(b) by 0 days.

(21) Appl. No.: 15/106,757

(22) PCT Filed: Dec. 16, 2014

(86) PCT No.: PCT/CN2014/093926
§ 371 (c)(1),
(2) Date: Jun. 20, 2016

(87) PCT Pub. No.: WO2015/096639
PCT Pub. Date: Jul. 2, 2015

(65) Prior Publication Data
US 2016/0311799 A1    Oct. 27, 2016

(30) Foreign Application Priority Data

Dec. 26, 2013 (CN) .......................... 2013 1 0733995
Dec. 6, 2014 (CN) .......................... 2014 1 0743073

(51) Int. Cl.
*C07D 209/86* (2006.01)
*C07D 401/14* (2006.01)

(52) U.S. Cl.
CPC ......... *C07D 401/14* (2013.01); *C07D 209/86* (2013.01)

(58) Field of Classification Search
CPC ........................... C07D 401/14; C07D 209/86

USPC ...................................................... 546/276.7
See application file for complete search history.

(56) References Cited

U.S. PATENT DOCUMENTS

| 2008/0145699 A1* | 6/2008 | Yabe | C07D 209/86 |
| | | | 428/690 |
| 2009/0236973 A1* | 9/2009 | Yabe | C07D 401/14 |
| | | | 313/504 |
| 2010/0327738 A1* | 12/2010 | Toba | C07D 401/10 |
| | | | 313/504 |

FOREIGN PATENT DOCUMENTS

| CN | 101076528 | * | 11/2007 |
| CN | 102503937 | * | 6/2012 |
| JP | 2009035524 A | | 2/2009 |
| JP | 2009141339 | * | 6/2009 |
| JP | 2011225498 | * | 11/2011 |
| WO | 2006/126542 A1 | | 11/2006 |

OTHER PUBLICATIONS

Su; J. Mater. Chem., 2012, 22, 3447-3456.*
Liu; Polym. Chem., 2011, 2, 1699-1705.*
First office action in Chinese patent application CN 201410743073.X dated Jan. 27, 2016.*
Su, S.J. et al., "Pyridine-Containing Bipolar Host Materials for Highly Efficient Blue Phosphorescent OLEDs", Chem. Mater., No. 5, vol. 20, Dec. 2, 2008, pp. 1691-1693, particular p. 1691, scheme 1.
Su, S.J. et al., "RGB Phosphorescent Organic Light-Emitting Diodes by Using Host Materials with Heterocyclic Cores: Effect of Nitrogen Atom Orientations", Chem. Mater., No. 2, vol. 23, Dec. 29, 2010, pp. 274-284, particular p. 276, scheme 1.

* cited by examiner

*Primary Examiner* — Noble Jarrell
*Assistant Examiner* — Daniel Carcanague
(74) *Attorney, Agent, or Firm* — Maschoff Brennan

(57) ABSTRACT

The present invention relates to "a method for synthesizing 2,6-bis[3'-(N-carbazolyl)phenyl]pyridine compound", and belongs to the field of chemical synthesis. In the present invention, a pyridine ring is formed by cyclization, the intermediate product can be directly used in the next reaction without purification and thus the process is very easy; the final product I will precipitate from the mixed reaction solution after the completion of the reaction, and the product can be very conveniently extracted.

13 Claims, No Drawings

METHOD FOR SYNTHESIZING 2,6-BIS[3'-(N-CARBAZOLYL)PHENYL] PYRIDINE COMPOUND

TECHNICAL FIELD

This invention relates to a chemical synthesis field, and in particular, to a non-palladium-catalyzed synthesis method of 2,6-bis[3'(N-carbazolyl)phenyl]pyridine compound.

BACKGROUND ART

Organic light-emitting devices (OLED), as a new type of display technology, have unique advantages such as self-illumination, wide viewing angle, low power consumption, high efficiency, thin, rich colors, fast response, extensive application temperature, low drive voltage, used to make flexible, bendable and transparent display panel and environmental friendliness, etc. Therefore, OLED technology can be applied to flat panel displays and new generation of lighting, or can be used as backlight of LCD. Since 1987, Kodak (Tang et al) made sandwich bilayer devices using 8-hydroxyquinoline aluminum (Alq3) as a light emitting layer, triphenylamine derivative as a hole transporting layer through thin-film vacuum evaporation technique. Under 10V driving voltage, the luminance is up to 1000 cd/m$^2$ (Tang C. W, Vanslyke S. A. Appl. Phys. Lett. 1987, 51, 913-916). This technological breakthrough has aroused widespread concern in the scientific community and industry, and organic light-emitting research and applications become a hot issue. Subsequently, in 1989, with the invention of host and guest material technology, the luminous efficiency and lifetime of OLED is greatly improved. In 1998, Ma Yuguang and Zhi Zhiming, et al found the electroluminescent phosphorescence phenomenon, which broke through the theoretical limit of organic electroluminescent quantum efficiency less than 25%, rising to 100% (Synthetic Metals 94 (1998) 245-248). Since then, the organic light-emitting entered into a new era, extending the field of research.

A classic OLED comprises a cathode and an anode, which includes a hole transport layer, a light emitting layer and an electron transport layer. The holes generating from the anode through the hole transport layer and the electrons generating from the cathode through the electron transport layer combine to form excitons in the light emitting layer, emitting light. 2,6-bis[3'-(N-carbazolyl)phenyl]pyridine (DCzPPy) was firstly developed by Kido and used as a bipolar host material in 2008; together with Flrpic, it is used in efficient blue phosphorescent organic light emitting diodes as a dopant (Chem. Mater. 2011, 23, 274-284). Jeong-Ik Lee made white-light OLED using DCzPPy. In combination with the unique molecular structures of carbazole electron donors with high triplet energy and eletron receptor pyridine with high electron affinity, DCzPPy is important bipolar host material of highly-efficient blue and white phosphorescent OLED (Adv. Mater. 2010, 22, 5003-5007).

The conventionally reported method for synthesis of DCzPPy (Chem. Mater. 2008,20,1691-1693) requires expensive palladium catalyst that may causes high production cost, and all experimental procedures require metal catalysts in the overall three-step synthesis steps, thereby increasing the risk of metal contamination of the final products. In addition, the intermediates and final products must be purified by column chromatography, difficult to be applied in mass production.

SUMMARY OF THE INVENTION

In order to solve the above problems, the present invention provides a simple and efficient method for preparing 2,6-bis[3'-(N-carbazolyl)phenyl]pyridine compound, which can effectively solve the existing problems and shortcomings in the prior art, presenting a good application prospect.

The synthesis method of 2,6-bis[3'-(N-carbazolyl)phenyl] pyridine compound, comprising the following steps:

(1) Prepare the compound with the formula 1, wherein R1, R2 are independently hydrogen, alkyl or aryl,

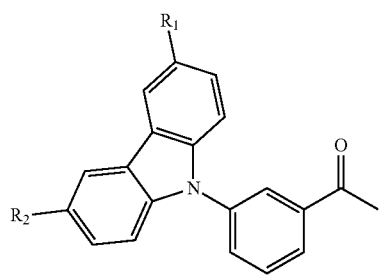

(2) The compound with the formula 1 reacts with N,N-dimethylformamide dimethyl acetal under a neutral condition or reacts with aromatic aldehyde under a strong alkaline condition to get the compound with the formula 2, wherein R3 is dimethylamino or aryl, the reaction is as follows:

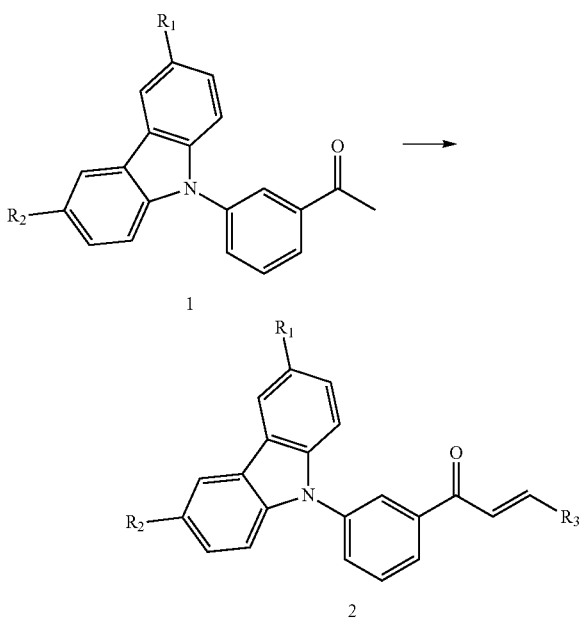

(3) The compounds with the formula 1, 2 reflux to react in the presence of acetic acid and ammonium acetate, to get the final product I, wherein R3' is hydrogen or aryl.

In the step (2), the formula 1 reacts with N,N-dimethylformamide dimethyl acetal under reflux condition for 12 hours, and concentrate to get the product.

In the step (2), the formula (1) and aromatic aldehyde have a solid phase mixed reaction in the presence of sodium hydroxide or potassium hydroxide.

The R1, R2 are hydrogen and alkyl groups; R₃ is dimethylamino, phenyl or pyridyl; R₃' is hydrogen, benzene or pyridine.

In the step (3), after reflux reaction 12-24 hours, the product I is separated out when the reaction mixture is cooled down, and filtered.

In the step (1), through Ullmann coupling reaction and using cuprous iodide as a catalyst and dimethyl formamide as the solvent, get the product according to the reflux reaction as below, wherein X is a halogen.

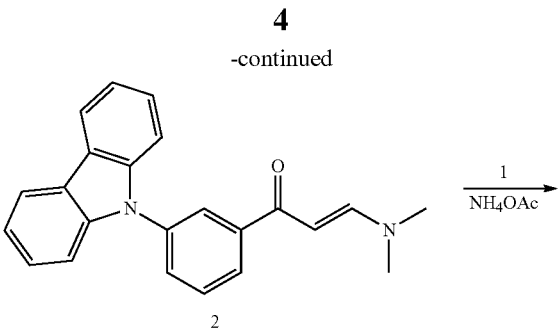

The X is bromine.

After complete reaction of the compound of formula 1, pour the reaction mixture into the ice water, separate out and filter.

For the purification of the compound of formula 1, after dried, the filtrate is dissolved in dichloromethane, filtered, and the filtrate is evaporated to dryness, to get oily matter, then soaked in methanol, to separate out the crystal.

In the present invention, the reactions are achieved mainly through the technical solutions as described in the following reaction formula:

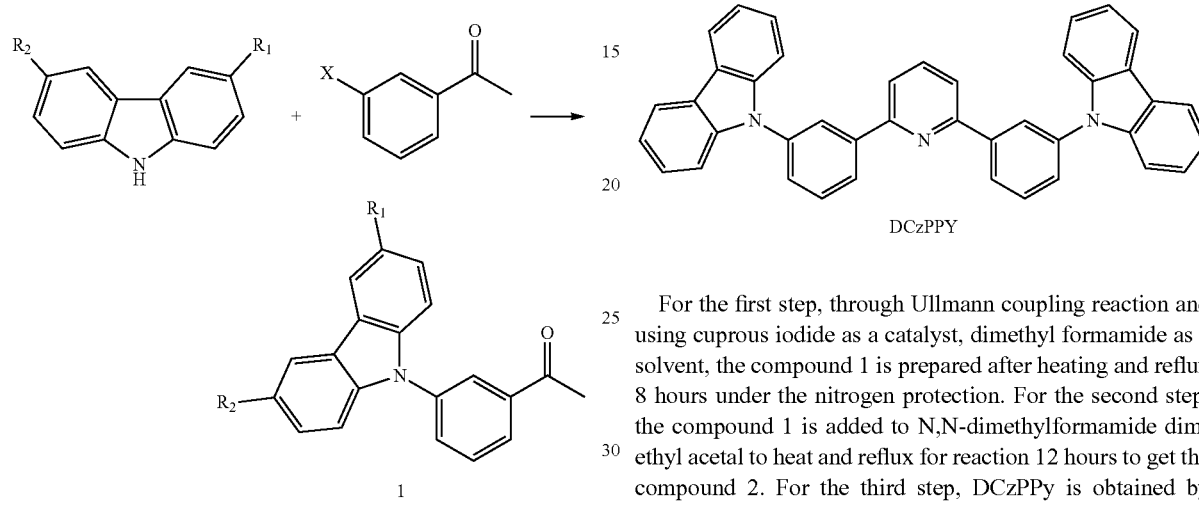

For the first step, through Ullmann coupling reaction and using cuprous iodide as a catalyst, dimethyl formamide as a solvent, the compound 1 is prepared after heating and reflux 8 hours under the nitrogen protection. For the second step, the compound 1 is added to N,N-dimethylformamide dimethyl acetal to heat and reflux for reaction 12 hours to get the compound 2. For the third step, DCzPPy is obtained by compounds 1 and 2 through ring-closure pyridine synthesis reaction. The intermediate compounds 1, 2 and the final product can be separated from the reaction mixture by filtration, without purification using column chromatography.

The preparation method in the invention can be extended to synthesize other 2,6-bis[3'-(N-carbazolyl)phenyl]pyridine derivatives (as shown in the following formula).

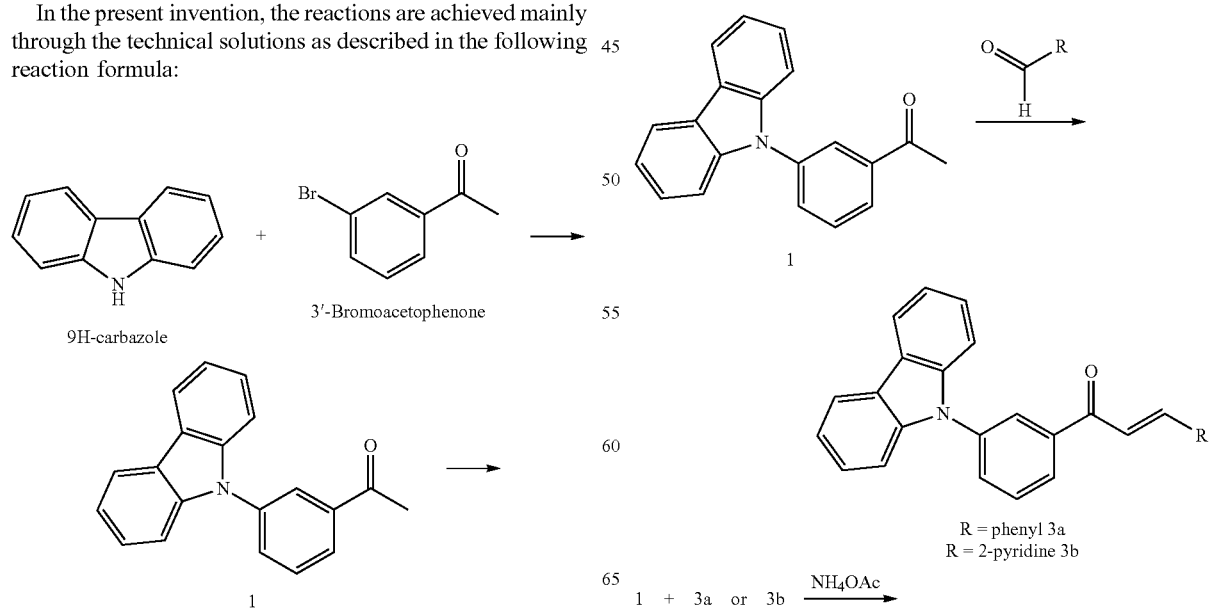

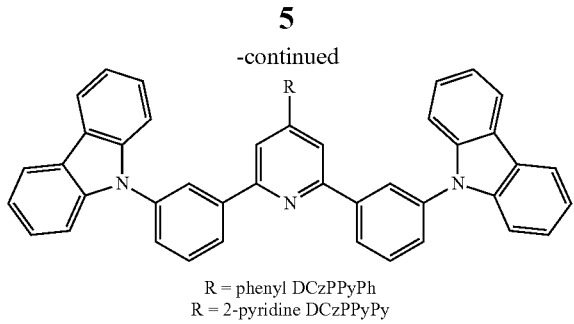

R = phenyl DCzPPyPh
R = 2-pyridine DCzPPyPy

The preparation method in the invention requires cyclization to form a pyridine ring. The obtained products 3a, 3b, 2 can be used directly in the next step without purification, which is very simple; and the final product I will be separated out of the reaction mixture after the completion of reactions, and it is very easy to extract the product.

DETAILED DESCRIPTIONS OF THE PREFERRED EMBODIMENTS

The invention is further described in details in conjunction with embodiments.

Embodiment 1 DCzPPy 1.1 Synthesis of Compound 1 (MB02-1) (Ref US20120305900-A1, US20110240968-A1)

Weigh carbazole (10 mmol), 3-bromoacetophenone (10 mmol), potassium carbonate (20 mmol), copper iodide (1 mmol), 1,10-phenanthroline (1 mmol) in a 100 mL three-neck flask with magnetic sticks, then vacuumize the device to remove oxygen and supply nitrogen. Add 18-crown-6 (0.3 mmol), 20 mL of dry dimethylformamide successively with the nitrogen protection, heat to the solvent reflux temperature to start reaction. After 36 hours of reaction, confirm that the starting reactants are basically completed to stop the reactions using TLC (developing solvent petroleum ether: dichloromethane=2:1). Pour the reaction solution in 500 mL of ice water to separate out a large amount of yellow precipitate, stand for 2 hours, then perform suction filtration under reduced pressure, and dry the filter cake in a vacuum drying oven at 40° C. Place the dried substance into dichloromethane solution to separate out pale yellow inorganic salt precipitate, then filter through sand core, spin-evaporate the collected filtrate to get the oily substance. Soak the oily substance in 10 mL of methanol, 5 hours later, white needle crystal is separated out, with the yield of 83% and HPLC purity of 99%. 1H NMR (400 MHz, CDCl3) δ 8.18 (s, 2H), 8.16 (s, 1H), 8.06 (d, J=7.7 Hz, 1H), 7.80 (d, J=7.8 Hz, 1H), 7.73 (t, J=7.7 Hz, 1H), 7.47-7.36 (m, 4H), 7.32 (t, J=7.3 Hz, 2H), 2.67 (s, 3H).

1.2 Synthesis of Compound 2 (MB02-2)

Take a reaction flask, a condenser, a heating stirrer to prepare the experimental apparatus. Add the compound 1 (1.75 mmol), N, N-dimethylformamide dimethyl acetal (10 mL) to the reaction vessel, then heat to the reflux temperature for reaction 12 h. When the reaction starts, the reaction solution is yellow. After reaction, reduce pressure and spin evaporate to get the target product, a yellow solid, with the yield of 97% and HPLC purity of 99%. 1H NMR (400 MHz, CDCl3) δ 8.16 (d, J=7.7 Hz, 2H), 8.08 (s, 1H), 8.02 (s, 1H), 7.87 (d, J=12.3 Hz, 1H), 7.66 (d, J=4.0 Hz, 2H), 7.41 (s, 4H), 7.30 (dd, J=7.6, 3.7 Hz, 2H), 5.70 (d, J=12.2 Hz, 1H), 3.17 (s, 3H), 2.90 (s, 3H).

1.3 Synthesis of Compound DCzPPy

Take a reaction flask, a condenser, a heating stirrer to prepare the experimental apparatus. Add MB02-1 (0.71 mmol), MB02-2 (0.71 mmol), potassium t-butoxide (1.05 mmol) successively to the reaction vessel to remove the oxygen in the vessel, and supply nitrogen. With the nitrogen protection, add anhydrous THF (10 mL) to stir 2 h at the room temperature, and the solution becomes orange-yellow. Add acetic acid (10 mL) and ammonium acetate (42 mmol) to the reactor, and the solution becomes orange-yellow, add the condenser, to react 2 h at the reflux temperature. As the reaction proceeds, solid substance is separated out, then the reaction is stopped, filtered to get the target product, with the yield of 88% and HPLC purity of 99%. 1H NMR (400 MHz, CDCl3) δ 8.34 (s, 2H), 8.25 (d, J=7.7 Hz, 2H), 8.17 (d, J=7.6 Hz, 4H), 7.88 (t, J=7.8 Hz, 1H), 7.77 (d, J=7.7 Hz, 2H), 7.72 (t, J=7.7 Hz,2H), 7.63 (d, J=7.8 Hz, 2H), 7.47 (d, J=8.1 Hz, 4H), 7.36 (t, J=7.6 Hz, 4H), 7.29 (d, J=7.5 Hz, 4H).

Embodiment 2 Synthesis of Compound DCzPPyPh

Add benzaldehyde (0.25 mmol), MB02-1 (0.5 mmol), sodium hydroxide (0.5 mmol) in a ceramic crucible (diameter of 6 cm) successively, after grinding 30 min, the reaction mixture state changes from solid powder to viscous state, then to solid powder. Transfer the ground solid powder to a round bottom flask, then add acetic acid (10 mL), ammonium acetate (1.5 mmol) respectively, heat to the reflux temperature and react overnight, to stop the reaction. As the reaction proceeds, solid substance is separated out, then the reaction is stopped, filtered to get the target product, with the yield of 82% and HPLC purity of 95%. 1H NMR (400 MHz, CDCl3) δ 8.34 (s, 2H), 8.25 (d, J=7.7 Hz, 2H), 8.17 (d, J=7.6 Hz, 4H), 7.88 (t, J=7.8 Hz, 1H), 7.77 (d, J=7.7 Hz, 2H), 7.72 (t, J=7.7 Hz,2H), 7.63-7.51 (m, 6H), 7.47 (d, J=8.1 Hz, 4H), 7.36 (t, J=7.6 Hz, 4H), 7.29 (d, J=7.5 Hz, 4H).

Example 3 Synthesis of Compound DCzPPyPy

Add 2-pyridyl carbaldehyde (0.25 mmol), MB02-1 (0.5 mmol), sodium hydroxide (0.5 mmol) in a ceramic crucible (diameter of 6 cm) successively, after grinding 30 min, the reaction mixture state changes from solid powder to viscous state, then to solid powder. Transfer the ground solid powder to a round bottom flask, then add acetic acid (10 mL), ammonium acetate (1.5 mmol) respectively, heat to the reflux temperature and react overnight, to stop the reaction. As the reaction proceeds, solid substance is separated out, then the reaction is stopped, filtered to get the target product, with the yield of 79% and HPLC purity of 95%. 1H NMR (400 MHz, CDCl3) δ 8.60 (d, J=7.4 Hz, 1H), 8.34 (s, 2H), 8.25 (d, J=7.7 Hz, 2H), 8.17 (d, J=7.6 Hz, 4H), 7.88-7.85 (m, 2H), 7.77 (d, J=7.7 Hz, 2H), 7.72 (t, J=7.7 Hz,2H), 7.63 (d, J=7.8 Hz, 2H), 7.47 (d, J=8.1 Hz, 4H), 7.36-7.32 (m, 5H), 7.29 (d, J=7.5 Hz, 4H). The above embodiments describe a simple and efficient method for preparing 2,6-bis[3'-(N-carbazolyl)phenyl]pyridine compound provided in the invention, which can replace the conventionally-used expensive palladium catalyst preparation method, to effectively reduce production costs and lower the risk of metal contamination of the final products. In the preparation method, the intermediates and final product are not required to be purified by column chromatography, suitable for mass production, having a good prospect.

The invention claimed is:

1. A method for synthesis of a 2,6-bis[3'-(N-carbazolyl)phenyl]pyridine compound of Formula I, Formula I

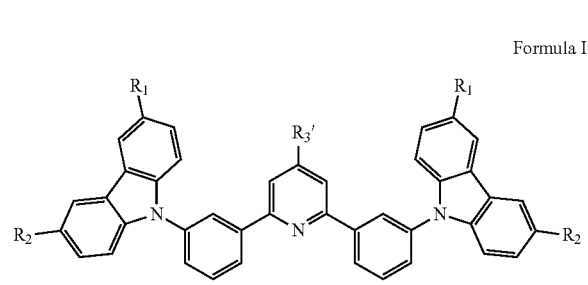

wherein $R_1$, $R_2$ are independently hydrogen, alkyl or aryl and $R_3'$ is hydrogen or aryl, the method comprising the following steps:

(1) reacting a 9H-carbazole compound and acetophenone compound to give a compound of formula 1 as shown in the following scheme:

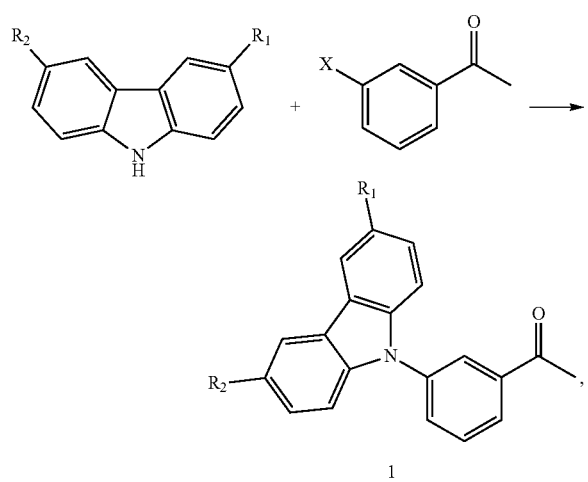

wherein X is halogen and $R_1$ and $R_2$ are independently hydrogen, alkyl or aryl, (2) reacting the compound of formula 1 with either N,N-dimethylformamide dimethyl acetal under a neutral condition or with an aromatic aldehyde under a strong alkaline condition to give a compound of formula 2, wherein $R_3$ is dimethylamino or aryl, as shown in following scheme:

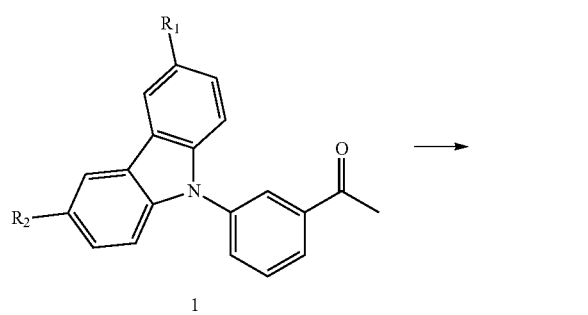

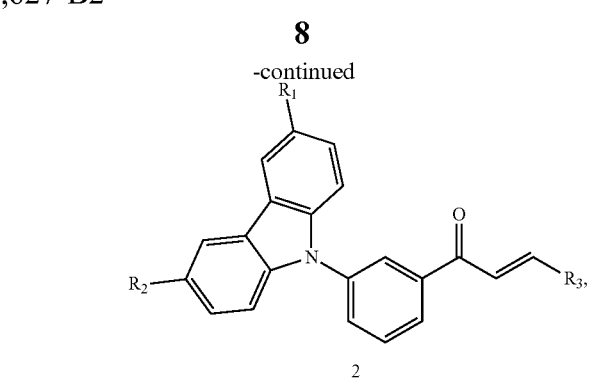

(3) combining the compounds of formula 2 with the compound of formula 1 in the presence of acetic acid and ammonium acetate and reacted under reflux to give the compound of Formula I as product.

2. The method according to claim 1, wherein, in the step (2), the compound of formula 1 is reacted with N,N-dimethylformamide dimethyl acetal under reflux condition for 12 hours, and the reaction mixture is concentrated to give the product.

3. The method according to claim 1, wherein, in the step (2), the compound of formula 1 is reacted with an aromatic aldehyde in the presence of sodium hydroxide or potassium hydroxide in a solid phase mixture, give the compound of formula 2.

4. The method according to claim 2, wherein $R_1$ and $R_2$ are hydrogen; $R_3$ is dimethylamino and $R_3'$ is hydrogen.

5. The method according to claim 4, wherein the reaction in step (3) is heated under reflux for 12-24 hours.

6. The method according to claim 5, wherein the reaction mixture is cooled down to separate out the product compound of Formula I, which is isolated by filtration.

7. The method according to claim 1, wherein, the compound of formula 1 is prepared in step (1) through Ullmann coupling reaction, using cuprous iodide as a catalyst and dimethyl formamide as the solvent, under reflux reaction to give a compound of formula 1, wherein X is a halogen, as shown in following scheme:

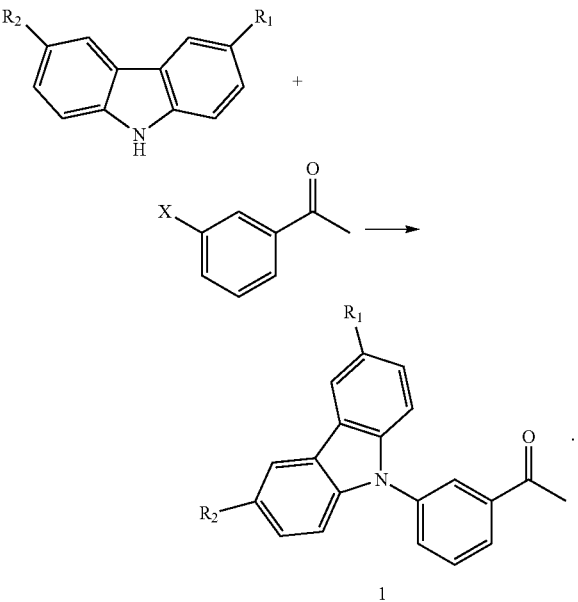

8. The method according to claim 7, wherein X is bromine.

9. The method according to claim 8, wherein, after the Ullman coupling reaction is complete, the compound of formula 1 is isolated by pouring the reaction mixture into the ice water, separating out and filtering.

10. The method according to claim 9, wherein the isolated compound of formula 1 is further purified, by drying and dissolving in dichloromethane, filtering, and evaporating solution to dryness, to produce an oily substance, which is then combined with methanol to separate out the compound of formula 1 as a crystalline solid.

11. The method according to claim 3, wherein $R_1$ and $R_2$ are hydrogen and $R_3$ and $R_3'$ are phenyl or pyridine.

12. The method according to claim 11, wherein the reaction in step (3) is heated under reflux for 12-24 hours.

13. The method according to claim 12, wherein the reaction mixture is cooled down to separate out the product compound of Formula I, which is isolated by filtration.

* * * * *